(12) United States Patent
Faust

(10) Patent No.: US 9,663,433 B2
(45) Date of Patent: May 30, 2017

(54) METHOD OF ALKYLATING OR ACYLATING AN ARENE

(71) Applicant: The University of Massachusetts, Boston, MA (US)

(72) Inventor: Rudolf Faust, Lexington, MA (US)

(73) Assignee: THE UNIVERSITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 15/196,096

(22) Filed: Jun. 29, 2016

(65) Prior Publication Data

US 2017/0001936 A1 Jan. 5, 2017

Related U.S. Application Data

(60) Provisional application No. 62/186,408, filed on Jun. 30, 2015.

(51) Int. Cl.

| | | |
|---|---|---|
| *C07C 45/46* | (2006.01) | |
| *C07C 2/86* | (2006.01) | |
| *C07C 37/18* | (2006.01) | |
| *B01J 31/00* | (2006.01) | |
| *B01J 31/22* | (2006.01) | |
| *B01J 31/14* | (2006.01) | |

(52) U.S. Cl.
CPC .............. *C07C 45/46* (2013.01); *B01J 31/143* (2013.01); *B01J 31/2213* (2013.01); *C07C 2/86* (2013.01); *C07C 37/18* (2013.01); *B01J 2231/44* (2013.01); *B01J 2531/31* (2013.01); *C07C 2531/14* (2013.01)

(58) Field of Classification Search
CPC . C07C 45/46; C07C 2/86; C07C 37/18; B01J 31/146; B01J 31/2213; B01J 2231/44; B01J 2531/31
See application file for complete search history.

(56) References Cited

PUBLICATIONS

Brown, et al, "Isomer Distribution and Partial Rate Factors in the Gallium Bromide Catlyzed Alkylation of Benzene and Toluene. The Selectivity Factor, Si, in Electrophilic Subsutitution" J. Am. Chem. Soc. vol. 78 (1956), 6255-6259.
Brown, et al.,"The Reaction of Benzene and Toluene with Methyl Bromide and Iodide in the Presence of Aluminum Bromide; Evidence for a Displacement Mechanism in the Methylation of Aromatic Compounds" J. Am. Chem. Soc. vol. 77(1955)5584-5589.
Chaturvedi, et al., "An efficient and novel approach for the synthesis of substituted N-aryl lactams" Organic Biomolecular Chemistry vol. 10 (2012), 9148-9151.
Elavarasan, et al., "Kinetics of phenol alkylation with tert-butyl alcohol using sulfonic acid functional ionic liquid catalysts" Chemical Engineering Journal vol. 166 (2011) 340-347.
Gold, et al., "Aromatic Alkylation. Part V. Alkylation by Aliphatic Alcohols in Aqueous Perchloric Acid" J. Amer. Chem. Soc. (1962), 4183-4188.
Jungk, et al., "Kinetics of Methylation and Ethylation of Benzene and Toluene in 1,2,4-Trichlorobenzene under the Influence of Aluminum Bromide; Mechanism of the Alkylation Reaction" J. Am. Chem. Soc. vol. 78 (1956), 2185-2190.
Kovacic, et al., "The ortho/para Ratio in Electrophilic Aromatic Substitution. Mercuration and Alkylation of Chlorobenzene and Anisole. Evidence for a Coordination Effect" J. Org. Chem. vol. 30 (1965), 1581-1588.
Kumar, et al., "Synthesis of Highly Reactive Polyisobutylene Catalyzed by EtAlCl2/Bis(2-chloroethyl) Ether Soluble Complex in Hexanes" Macromolecules, vol. 47 (2014), 1959-1965.
Lu, et al., "Effect of controlled SiO2 desposition and phosphorus and nickel doping on surace acidity and diffusivity of medium and small sized HZSM-5 for para-selective alkylation of toluene by methanol" Applied Catalsyis A: General vol. 453 (2013) 302-309.
Moghaddam, et al. "A New Eco-Friendly and Efficient Mesoporous Solid Acid Catalyst for the Alkylation of Phenols and Naphthols Under Microwave Irradiation and Solvent-Free Conditions" Trans. C Chem. Chem. Eng. vol. 16, (2009), 81-88.
Ojwach et al., "(Pyrazol-1-ylmethyl)pyridine Nickel Complexes: Ethylene Oligomerization and Unusual Friedel-Crafts Alkylation Catalysts" Organometallics vol. 28 (2009), 2127-2133.
Olah, et al., "Boron, Aluminum, and Gallium Tris(trifluoromethanesulfonate) (Triflate): Effective New Fridel-Crafts Catalysts" Journal Am. Chem. Soc. vol. 110 (1988), 2560-2565.
Olah, et al., "Friedel-Crafts Alkylation of Anisole and Its Comparison with Toluene. Predominant Ortho-Para Substitution under Kinetic Conditions and the Effect of Thermodynamic Isomerizations" Journal Am. Chem. Soc. vol. 106, No. 18 (1984), 5284-5290.
Smoot, et al., "Kinetics and Relative Rates of the Gallium Bromide Catalyzed Reactions of Alklyl Bromides with Aromatics" Journal Am. Chem. Soc. vol. 78 (1956), 6249-6254.
Stang, et al., "Preparation and Chemistry of Vinyl Triflates. 16. Mechanism of Alkylation of Aromatic Substrates" J. Am. Chem. Soc. vol. 100 (1978), 1520-1525.
Stock, et al., "Rates of Bromination of Anisole and Certain Derivatives. Partial Rate Factors for the Bromination Reaction. The Application of the Selectivity Relationship to the Subsitition REactions of Anisole" Journal Am. Chem. Soc. vol. 82 (1960), 1942-1947.

(Continued)

*Primary Examiner* — Sikarl Witherspoon
(74) *Attorney, Agent, or Firm* — Cantor Colburn LLP

(57) ABSTRACT

A method of alkylating or acylating an arene includes reacting the arene with an organic halide in the presence of an aprotic solvent and a catalyst of formula (I)

$$MR^1_m X_n \cdot Z(R^2)(R^3) \tag{I}$$

wherein M is Al, Ga, or Fe; $R^1$ is $C_1$-$C_{12}$ alkyl; m is 0 or 1; $R^2$ and $R^3$ are each independently unsubstituted or substituted $C_2$-$C_{12}$ alkyl; each occurrence of X is independently a halogen; n is 2 or 3; the sum of m and n is 3; and Z is S or O. When M is Al, then m is 1, n is 2, and $R^2$ and $R^3$ are each independently substituted with at least one electron-withdrawing group. When M is Ga or Fe, then m is 0 and n is 3.

14 Claims, 13 Drawing Sheets

(56) References Cited

PUBLICATIONS

Wolovsky, et al., "Facile Cycloalkylation of Benzene with Cyclododecene or Cyclopentadecene using Ethylaluminum Dichloride as Catalyst" Synthesis (1970), 656-657.

METHOD OF ALKYLATING OR ACYLATING AN ARENE

CROSS REFERENCE TO RELATED APPLICATIONS

This application claims the benefit of U.S. Provisional Application No. 62/186,408, filed 30 Jun. 2015, which is incorporated by reference herein in its entirety.

BACKGROUND OF THE INVENTION

Alkylation of toluene or phenol is a typical Friedel-Crafts reaction that is important in industry due to the wide application of the alkylated products. Among the alkylated isomers, the para-counterpart such as para-alkylated toluene or phenol is highly desirable for industrial applications as essential feedstock for antioxidants, phenolic resins, ultraviolet absorbers, varnishes and heat stabilizers in polyolefins. P. Elavarasan, K. Kondamudi, S. Upadhyayula, *Chem. Eng. 1* 2011, 166, 340-347. 4-tert-butylphenol is used to make oils and phosphate esters. F. M. Moghaddam, M. Akhlaghi, L. Hojabri, M. G. Dekamin, *Trans. C Chem. Chem. Eng.* 2009, 16, 81-88. Thus, efficient and selective alkylation, to yield para-substituted alkyl aromatics has received tremendous interest in recent years. P. Lu, Z. Fei, L. Li, X. Feng, W. Ji, W. Ding, Y. Chen, W. Yang, Z. Xie, *Appl. Catal., A* 2013, 453, 302-309.

In the course of more than 100 years of Friedel-Crafts chemistry, considerable work has been done on aromatic alkylations utilizing Friedel-Crafts chemistry. G. A. Olah, Friedel-Crafts Chemistry; Wiley-Interscience: New York, 1973. Olah and coworkers reported Friedel-Crafts alkylation of anisole and toluene using metal halides such as $AlCl_3$ and $BF_3$. G. A. Olah, J. A. Olah, T. Ohyama, *J. Am. Chem. Soc.* 1984, 106, 5284-5290. The same group subsequently reported boron, aluminum, and gallium triflates as convenient and effective new Friedel-Crafts catalysts for alkylation of benzene and toluene. G. A. Olah, O. Farooq, S. M. F. Farnia, J. A. Olah, *J. Am. Chem. Soc.* 1988, 110, 2560-2565. However, the para-selectivity was poor due to rapid isomerization to a more thermodynamically favored meta isomer. Brown et al. obtained 10% meta substitution in methylation (C. R. Smoot, H. C. Brown, *J. Am. Chem. Soc.* 1956, 78, 6249-6254), 21% in ethylation (L. M. Stock, H. C. Brown, *J. Am. Chem. Soc.* 1960, 82, 1942-1947), 27% in isopropylation (H. C. Brown, H. Jungk, *J. Am. Chem. Soc.* 1955, 77, 5584-5589), 32% in tert-butylation (H. Jungk, C. R. Smoot, H. C. Brown, *J. Am. Chem. Soc.* 1956, 78, 2185-2190), and 21% in benzylation (H. C. Brown, C. R. Smoot, *J. Am. Chem. Soc.* 1956, 78, 6255-6259) in Friedel-Crafts alkylations of toluene. Gold and Riley reported the 60% perchloric acid catalyzed alkylation of anisole with alcohols and observed 45% ortho- and 55% para-alkylation with isopropyl alcohol and 20% ortho- and 80% para-alkylation with tent-butyl alcohol. V. Gold, T. Riley, *J. Chem. Soc.* 1962, 4183-4188. Kovacic and Hiller reported that alkylation of anisole with tert-butyl chloride (t-BuCl) gave 6% meta and 94% para isomer. P. Kovacic, J. J. Hiller, *J. Org. Chem.* 1965, 30, 1581-1588. Stang and Anderson studied the alkylation with vinyl triflates in the presence of a sterically hindered non-nucleophilic base 2,6-di-tert-butyl-4-methylpyridine producing 11% ortho and 89% para isomer for anisole alkylation and 28% ortho, 8% meta and 64% para isomer for toluene. P. J. Stang, A. G. Anderson, *J. Am. Chem. Soc.* 1978, 100, 1520-1525. Thus, it has been difficult to achieve high conversion retaining high para selectivity during alkylation of toluene and phenol. $EtAlCl_2$ has been employed in cycloalkylation of benzene (R. Wolovsky, N. Maoz, Z. Nir, *Synthesis* 1970, 656-657) and alkylation of substituted arenes, but only in polar solvents such as dichloromethane (D. Chaturvedi, A. K. Chaturvedi, N. Mishra, V. Mishra, *Org. Biomol. Chem.* 2012, 10, 9148-9151).

There remains a need for Friedel-Crafts methods exhibiting high regioselectivity and conversion.

BRIEF SUMMARY OF EMBODIMENTS OF THE INVENTION

One embodiment is a method of alkylating or acylating an arene, the method comprising: reacting an arene with an organic halide selected from the group consisting of unsubstituted or substituted tertiary alkyl halides, unsubstituted or substituted allyl halides, unsubstituted or substituted benzyl halides, and unsubstituted or substituted acyl halides in the presence of a catalyst and an aprotic solvent; wherein the catalyst is of formula (I)

$$MR^1{}_m X_n \cdot Z(R^2)(R^3) \qquad (I)$$

wherein M is Al, Ga, or Fe; $R^1$ is $C_1$-$C_{12}$ alkyl; m is 0 or 1; $R^2$ and $R^3$ are each independently unsubstituted or substituted $C_2$-$C_{12}$ alkyl; each occurrence of X is independently a halogen; n is 2 or 3; the sum of m and n is 3; and Z is S or O; provided that when M is Al, then m is 1, n is 2, and $R^2$ and $R^3$ are each independently substituted with at least one electron-withdrawing group; and provided that when M is Ga or Fe, then m is 0 and n is 3.

This and other embodiments are described in detail below.

DETAILED DESCRIPTION OF THE INVENTION

Figure 1:
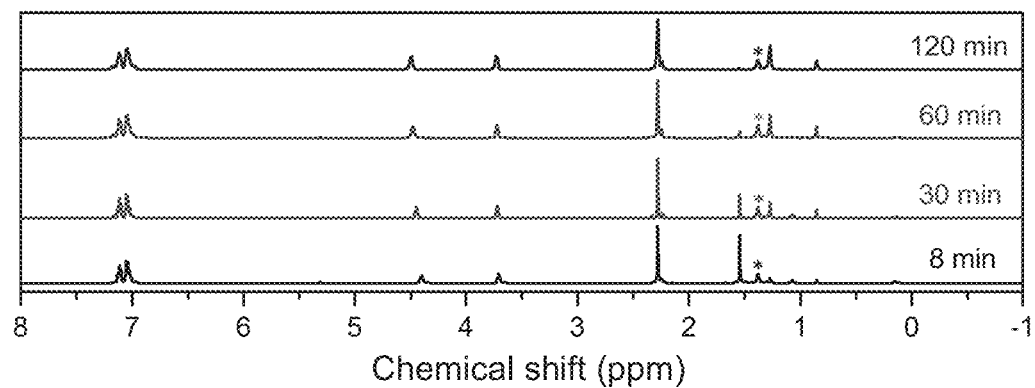
FIG. 1 shows representative proton nuclear magnetic resonance ($^1$H NMR spectra for the reaction of toluene with tert-butyl chloride (t-BuCl) in presence of a complex of ethyl aluminum dichloride with bis(2-chloroethyl) ether (EADC·CEE) at different times at 0° C. in cyclohexane-$d_{12}$. Initial conditions: [t-BuCl]=0.05 M, [EADC·CEE]=0.05 M, [CEE]/[EADC]=1. An asterisk (*) denotes the cyclohexane-$d_{11}$H resonance.

Due to the limited solubility of the traditional catalysts, Friedel-Crafts reactions generally do not readily proceed in non-polar solvents. When hexane was used as solvent, only trace amounts of alkylated toluene products were observed using (pyrazol-1-ylmethyl)pyridine Ni complexes. S. O. Ojwach, I. A. Guzei, L. L. Benade, S. F. Mapolie, J. Darkwa, *Organometallics* 2009, 28, 2127-2133. Therefore, investigation of Friedel-Crafts reactions in non-polar solvents is of high importance. In the course of mechanistic studies on the polymerization of isobutylene (IB) using EtAlCl$_2$/bis(2-chloroethyl) ether (EADC·CEE) complex in hexane, alkylation of toluene with t-BuCl as a side reaction was observed. Thus, we undertook an investigation of Friedel-Crafts alkylation and acylation of arenes in non-polar solvent using complexes of Lewis acids and Lewis bases.

One embodiment is a method of alkylating or acylating an arene, the method comprising: reacting an arene with an organic halide selected from the group consisting of unsubstituted or substituted tertiary alkyl halides, unsubstituted or substituted allyl halides, unsubstituted or substituted benzyl halides, and unsubstituted or substituted acyl halides in the presence of a catalyst and an aprotic solvent; wherein the catalyst is of formula (I)

$$MR^1{}_mX_n\cdot Z(R^2)(R^3) \qquad (I)$$

wherein M is Al, Ga, or Fe; R$^1$ is C$_1$-C$_{12}$ alkyl; m is 0 or 1; R$^2$ and R$^3$ are each independently unsubstituted or substituted C$_2$-C$_{12}$ alkyl; each occurrence of X is independently a halogen; n is 2 or 3; the sum of m and n is 3; and Z is S or O; provided that when M is Al, then m is 1, n is 2, and R$^2$ and R$^3$ are each independently substituted with at least one electron-withdrawing group; and provided that when M is Ga or Fe, then m is 0 and n is 3.

The arene that is alkylated or acylated can have one or more aromatic rings. When the arene has two or more aromatic rings, any two of the rings can be fused or not fused. In some embodiments, the arene is an unsubstituted or substituted C$_6$-C$_{18}$ arene. In the context of the arene, the term "substituted" means having one or more substituents selected from monovalent substituents including hydroxyl, C$_1$-C$_{12}$ alkyl (including linear and branched alkyl), C$_3$-C$_{12}$ cycloalkyl, C$_2$-C$_{12}$ alkenyl, C$_2$-C$_{12}$ alkynyl, C$_1$-C$_{12}$ alkoxyl, C$_1$-C$_{12}$ amido (including N-monoalkylamido and N,N-dialkylamido), C$_2$-C$_{12}$ ether, C$_2$-C$_{12}$ ester, cyano, cyanato, thiocyanato, isocyanato, isothiocyanato, and nitro; and divalent substituents including C$_1$-C$_{12}$ alkylene, C$_3$-C$_{12}$ cycloalkylene, C$_2$-C$_{12}$ alkenylene, C$_2$-C$_{12}$ alkynylene, carbonyl (—C(O)—), divalent ester (—C(O)—O—), and divalent C$_1$-C$_{12}$ amide (—C(O)—N(R)—, wherein R is H or C$_1$-C$_{11}$ alkyl).

In some embodiments, the arene is an unsubstituted or substituted benzene. In some embodiments, the arene is a monosubstituted benzene. As demonstrated in the working examples, the method provides selective alkylation of monosubstituted benzenes in the para position.

The arene is reacted with an organic halide that is an alkylating agent or an acylating agent. Examples of organic halides include unsubstituted or substituted tertiary alkyl halides, unsubstituted or substituted allyl halides, unsubstituted or substituted benzyl halides, and unsubstituted or substituted acyl halides. In the context of the organic halide, the term "substituted" means having one or more substituents selected from monovalent substituents including cyano, cyanato, thiocyanato, isocyanato, isothiocyanato, and nitro. In some embodiments, the organic halide is selected from the group consisting of C$_4$-C$_{12}$ tertiary alkyl chlorides, allyl chlorides, benzyl chlorides, and C$_2$-C$_{12}$ acyl chlorides. In some embodiments, the organic halide is t-butyl chloride or acetyl chloride.

The reaction of the arene with the organic halide occurs in the presence of an aprotic solvent. An aprotic solvent is a solvent that does not have a hydrogen atom bound to an oxygen atom or to a nitrogen atom. In some embodiments, the aprotic solvent is an aliphatic aprotic solvent. In some embodiments, the aprotic solvent is a C$_5$-C$_{12}$ alkane.

The reaction of the arene with the organic halide also occurs in the presence of a catalyst. The catalyst is of formula (I)

$$MR^1{}_mX_n\cdot Z(R^2)(R^3) \qquad (I)$$

wherein M is Al, Ga, or Fe; R$^1$ is C$_1$-C$_{12}$ alkyl; m is 0 or 1; R$^2$ and R$^3$ are each independently unsubstituted or substituted C$_2$-C$_{12}$ alkyl; each occurrence of X is independently a halogen; n is 2 or 3; the sum of m and n is 3; and Z is S or O; provided that when M is Al, then m is 1, n is 2, and $R^2$ and $R^3$ are each independently substituted with at least one electron-withdrawing group; and provided that when M is Ga or Fe, then m is 0 and n is 3. The formula (I) structure is a complex of a Lewis acid, $MR^1{}_mX_n$, and a Lewis base, $Z(R^2)(R^3)$. In some embodiments, M is Al, $R^1$ is ethyl, and each occurrence of X is chloro; i.e., the Lewis acid is $EtAlCl_2$. In some embodiments, Z is O; i.e., the Lewis base is an ether. In some embodiments, M is Al, Z is O, and the at least one electron-withdrawing group is a halogen. In a subset of these embodiments, M is Al, Z is O, and the at least one electron-withdrawing group is chloro. In a preferred embodiment, M is Al, $R^1$ is ethyl, each occurrence of X is chloro, Z is O, and $R^2$ and $R^3$ are $-CH_2CH_2Cl$.

Having chosen an arene, an organic halide, a solvent, and a catalyst, a person skilled in the art can determine other reaction conditions—such as temperature and reagent concentrations—without undue experimentation. For example, when the arene is a monoalkyl-substituted benzene, the organic halide is an unsubstituted tertiary alkyl halide, and the solvent comprises n-hexane, the reaction can be conducted at a temperature of −10 to +10° C.

The invention includes at least the following embodiments.

Embodiment 1

A method of alkylating or acylating an arene, the method comprising: reacting an arene with an organic halide selected from the group consisting of unsubstituted or substituted tertiary alkyl halides, unsubstituted or substituted allyl halides, unsubstituted or substituted benzyl halides, and unsubstituted or substituted acyl halides in the presence of a catalyst and an aprotic solvent; wherein the catalyst is of formula (I)

$$MR^1{}_mX_n \cdot Z(R^2)(R^3) \quad \text{(I)}$$

wherein M is Al, Ga, or Fe; $R^1$ is $C_1$-$C_{12}$ alkyl; m is 0 or 1; $R^2$ and $R^3$ are each independently unsubstituted or substituted $C_2$-$C_{12}$ alkyl; each occurrence of X is independently a halogen; n is 2 or 3; the sum of m and n is 3; and Z is S or O; provided that when M is Al, then m is 1, n is 2, and $R^2$ and $R^3$ are each independently substituted with at least one electron-withdrawing group; and provided that when M is Ga or Fe, then m is 0 and n is 3.

Embodiment 2

The method of embodiment 1, wherein the arene is an unsubstituted or substituted $C_6$-$C_{18}$ arene.

Embodiment 3

The method of embodiment 1, wherein the arene is an unsubstituted or substituted benzene.

Embodiment 4

The method of embodiment 1, wherein the arene is a monosubstituted benzene.

Embodiment 5

The method of any one of embodiments 1-4, wherein the organic halide is selected from the group consisting of $C_4$-$C_{12}$ tertiary alkyl chlorides, allyl chloride, benzyl chloride, and $C_2$-$C_{12}$ acyl chlorides.

Embodiment 6

The method of any one of embodiments 1-4, wherein the organic halide is t-butyl chloride or acetyl chloride.

Embodiment 7

The method of any one of embodiments 1-6, wherein the aprotic solvent is an aliphatic aprotic solvent.

Embodiment 8

The method of any one of embodiments 1-6, wherein the aprotic solvent is a $C_5$-$C_{12}$ alkane.

Embodiment 9

The method of any one of embodiments 1-8, wherein M is Al, $R^1$ is ethyl, and each occurrence of X is chloro.

Embodiment 10

The method of any one of embodiments 1-9, wherein Z is O.

Embodiment 11

The method of any one of embodiments 1-9, wherein M is Al, Z is O, and the at least one electron-withdrawing group is a halogen.

Embodiment 12

The method of any one of embodiments 1-9, wherein M is Al, Z is O, and the at least one electron-withdrawing group is chloro.

Embodiment 13

The method of any one of embodiments 1-8, wherein M is Al, $R^1$ is ethyl, each occurrence of X is chloro, Z is O, and $R^2$ and $R^3$ are $-CH_2CH_2Cl$.

Embodiment 14

The method of embodiment 13, wherein the arene is a monoalkyl-substituted benzene, wherein the organic halide is an unsubstituted tertiary alkyl halide, wherein the solvent comprises n-hexane, and wherein said reacting is conducted at a temperature of −10 to +10° C.

All ranges disclosed herein are inclusive of the endpoints, and the endpoints are independently combinable with each other. Each range disclosed herein constitutes a disclosure of any point or sub-range lying within the disclosed range.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

The invention is further illustrated by the following non-limiting examples.

WORKING EXAMPLES

Materials. Tert-butyl chloride (t-BuCl, 98%, TCI America) and acetyl chloride (AcCl, >99%, Fluka) were used as received. Ethylaluminum dichloride (EADC, 25.7 weight percent solution in toluene), EADC (1.0 M solution in hexane), bis(2-chloroethyl) ether (CEE, 99%), potassium hydroxide (KOH, 90%), sodium hydroxide (NaOH, ≥98%), sodium sulfate ($Na_2SO_4$), 2-propanol (IPA, ≥99.5%), sodium acetate (NaOAc, 99%), ethylenediaminetetraacetic acid (EDTA, ≥98.5%) and dithizone (85%) were purchased from Aldrich and used without any further purification. Ammonium acetate ($NH_4OAC$) and zinc sulfate heptahydrate ($ZnSO_4 7H_2O$) were purchased from Fisher Scientific and used as received. 4-tert-Butyltoluene (>95.0%), 4-tert-butylphenol (>98.0%), 4'-methylacetophenone (>95.0%), 4'-hydroxyacetophenone (>98.0%) were purchased from TCI America and used as received.

Hexanes, mixture of isomers (Hex, Sigma-Aldrich, ≥98.5%, ACS reagent), was freed from olefinic impurities by refluxing over concentrated sulfuric acid for 48 hours. It was then washed with aqueous solution of KOH (10 weight percent) three times followed by washing with distilled water until neutral to pH paper. Then it was kept over anhydrous $Na_2SO_4$ overnight at room temperature and finally distilled over $CaH_2$ under a nitrogen atmosphere twice before use in the Friedel-Crafts reaction Preparation of EADC·CEE Complex. Complexes of EADC and CEE ([CEE]/[EADC]=1) were prepared just before use in the reaction. For this, first, the concentration of Al in the EADC in toluene and EADC in hexane (purchased from Aldrich) was determined. Then inside a glove box, an equimolar amount of CEE was added to the EADC solution and vortexed to form a 1.8 M Lewis acid/ether complex while using EADC solution in toluene, and a 0.996 M Lewis acid/ether complex while using EADC solution in hexane. The required amount of the complex was then added to 1.0 mL cyclohexane-$d_{12}$ to make the final concentration of the Lewis acid/ether complex at 0.05 M.

Determination of Al Content of EADC. Typically, 1 mL EADC solution was taken up in a 20 mL sealed vial inside the glove box. The vial was taken out of the glove box and EADC was dissolved in de-ionized water by adding dilute HCl and by refluxing. The solution was allowed to cool to room temperature. 15 mL of the standardized 0.05 M of EDTA solution was added into the beaker containing the decomposed EADC solution. The solution was diluted with 50 mL of de-ionized water. The pH was adjusted to 5 with dilute NaOH. 10 mL of sodium acetate buffer was added to the solution, refluxed for 3 minutes and allowed to cool to room temperature. Then 10 mL of ammonium acetate, 75 mL of 2-propanol and 1 mL of dithizone indicator solution were added. The solution was titrated against a standard 0.02 M $ZnSO_4$ solution to a pink end point to give the concentration of Al.

General Method for Alkylation using EADC·CEE complex. In a typical experiment, alkylation of phenol was carried out in cyclohexane-$d_{12}$ at 25° C. using the following initial concentrations of reactants: [Phenol]=0.05 M, [EADC·CEE]=0.05 M and [t-BuCl]=0.05 M. 50 µL of 1.0 M EADC·CEE complex was added to a solution containing 5 µL phenol and 1.0 mL cyclohexane-$d_{12}$ at 25° C. in a MBraun MB200MOD stainless steel glove box (Innovative Technology Inc.) equipped with a gas purification system (molecular sieves and copper catalyst) under dry nitrogen atmosphere. It was vortexed to mix the components and kept at 25° C. t-BuCl (5 µl) was added to it to start the reaction at 25° C. The progress of the reaction was monitored by taking $^1H$ NMR spectrum of the reaction mixture at different times at 25° C. It was thereafter quenched with chilled methanol. Isomer distribution was determined by GC-MS analysis. Alkylation of toluene was carried out as described in case of phenol.

General Method for Acylation using EADC·CEE complex. In a typical experiment, acylation of phenol was carried out in cyclohexane-$d_{12}$ at 25° C. using the following initial concentrations of reactants: [Phenol]=0.05 M, [EADC·CEE]=0.05 M and [AcCl]=0.05 M. 50 µL of 1.0 M EADC·CEE complex was added to a solution containing 5 µL phenol and 1.0 mL cyclohexane-$d_{12}$ at 25° C. in a MBraun MB200MOD stainless steel glove box (Innovative Technology Inc.) equipped with a gas purification system (molecular sieves and copper catalyst) under dry nitrogen atmosphere. It was vortexed to mix the components and kept at 25° C. AcCl (4 µL) was added to it to start the reaction at 25° C. AcCl (4 µL) was added to it to start the reaction. The progress of the reaction was monitored by taking $^1H$ NMR spectrum of the reaction mixture at different times at 25° C. It was thereafter quenched with chilled methanol. Isomer distribution was determined by GC-MS analysis. Acetylation of toluene was carried out using similar procedure.

Characterization. Nuclear Magnetic Resonance (NMR) Spectroscopy. Proton nuclear magnetic resonance CH NMR) spectra were recorded on a Bruker 500 MHz spectrometer using cyclohexane-$d_{12}$ as solvent (Cambridge Isotope Laboratory, Inc.).

Attenuated Total Reflectance Fourier Transform Infrared Spectroscopy (ATR-FTIR). ATR-FTIR spectra were taken using a Mettler Toledo React IR 4000 instrument equipped with a DiComp probe connected to an MCT detector with a K6 conduit in the spectral range from 4000 to 650 $cm^{-1}$ at a resolution of 2 $cm^{-1}$.

Gas Chromatography-Mass Spectrometry Analysis. The gas chromatography-mass spectrometry (GC-MS) analysis of all the products was performed using an Agilent 7890A (GC)-Agilent 5975 C inert MSD with triple axis detector and an Agilent 7693 autosampler from Agilent Technologies. The temperatures of the transfer line, the quadrupole and the ion source were set at 320, 150 and 230° C., respectively. The system was operated by Agilent MSD ChemStation E.02.00.493 software. Separation was carried out on a nonpolar DB-5 capillary column (Agilent) with length=30 meter, ID=0.250 mm, film thickness=0.25 um for toluene alkylation samples and a polar crossbond PEG column (RESTEK USA cat #12423, serial #503025) with length=30 meter, ID=0.250 mm, film thickness=0.25 µm for phenol alkylation samples. Helium (purity 99.999%) was employed as carrier gas at a constant column flow of 1.0 mL $min^{-1}$. The GC oven temperature was programmed from 60° C. (held for 2 min) to 140° C. at 10° C. $min^{-1}$ (held for 1 min) for toluene alkylation samples, and programmed from 60° C. (held for 3 min) to 220° C. at 10° C. $min^{-1}$ (held for 1 min) for phenol alkylation samples. The injector temperature was kept at 260° C. The injection volume was 2 µL. For acetylation products, separation was carried out on a polar crossbond PEG column (RESTEK USA cat #12423, serial #503025) with length=30 meter, ID=0.250 mm, film thickness=0.25 µm for phenol alkylation samples. The GC oven temperature was programmed from 60° C. (held for 0 min) to 180° C. at 10° C. min$^{-1}$ (held for 0 min) for toluene acetylation samples and from 60° C. (held for 3 min) to 220° C. at 10° C. min$^{-1}$ (held for 1 min) for phenol acetylation samples.

Figure 2:
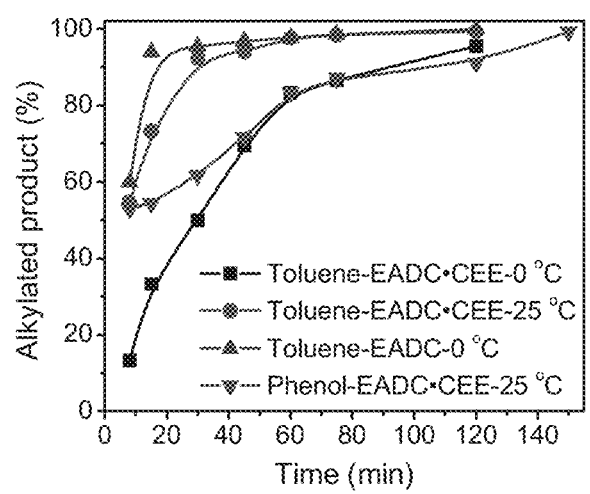
FIG. 2 is a plot of conversion of t-BuCl to the alkylated product during Friedel-Craft alkylation reaction of toluene and/or phenol in presence of t-BuCl in cyclohexane-$d_{12}$, calculated from the respective $^1$H NMR spectra at different time.

The alkylation of toluene with t-BuCl was studied using EADC·CEE complex at 0 and 25° C., and using just EADC at 0° C. in cyclohexane-d$_{12}$. The progress of the reaction was monitored by $^1$H NMR spectroscopy. FIG. 1 depicts typical $^1$H NMR spectra during alkylation of toluene at 0° C. at different times. FIG. 1 shows a decrease of the intensity of the methyl resonance at 1.6 ppm (corresponding to t-BuCl) and increase of the methyl resonance at 1.3 ppm (corresponding to tert-butyltoluene) with time. Quantitative conversions were observed in 2 hours (Table 1). The conversion of t-BuCl to the alkylated toluene is plotted as a function of time in FIG. 2 based on the integrations of the corresponding proton signals. According to FIG. 2, alkylation of toluene is much faster at 25° C. compared to that at 0° C. Furthermore, alkylation of toluene using just EADC at 0° C. is much faster than that using EADC·CEE complex at 0° C.

after 2.5 hours. From the fragmentation pattern and the molecular ion peak 135 of the GC-MS spectrum (FIG. 8), the species at 9.55 min (FIG. 7) was confirmed to be 4-tert-butylphenol. Thus, GC-MS result confirms the exclusive para selective alkylation of phenol in presence of t-BuCl using EADC·CEE complex at 25° C. (Table 1, entry 4).

Figure 9:
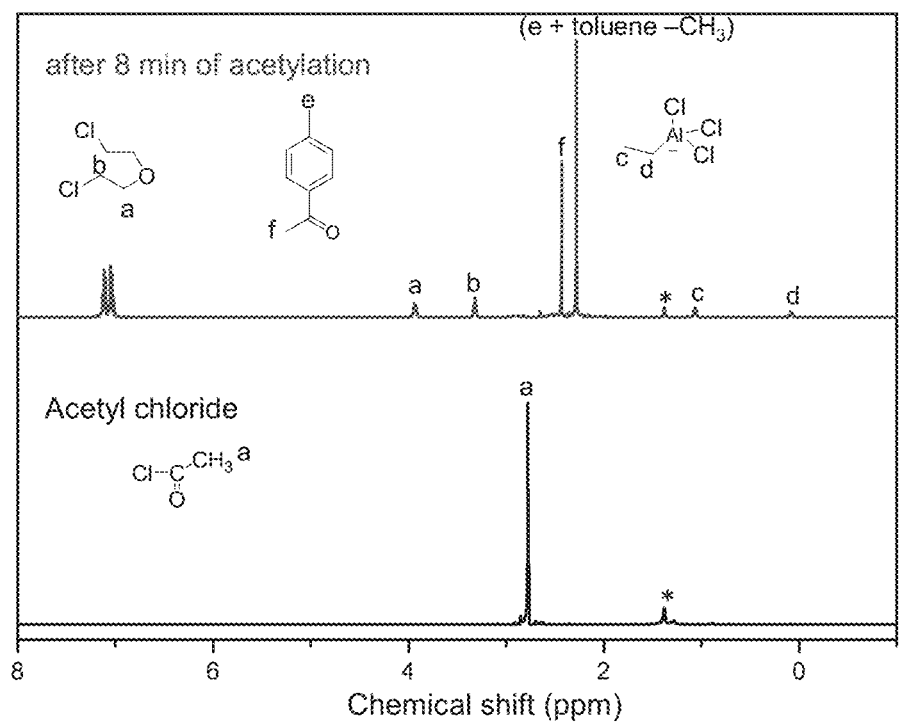
FIG. 9 shows $^1$H NMR spectra of acetyl chloride (bottom), and [EADC·CEE+AcCl] in the presence of toluene after 8 minutes of acetylation at 0° C. in cyclohexane-d$_{12}$ (top). Initial conditions: [AcCl]=0.05 M, [EADC·CEE]=0.05 M, [CEE]/[EADC]=1. An asterisk (*) denotes the cyclohexane-d$_{11}$H resonance.
Figure 10:
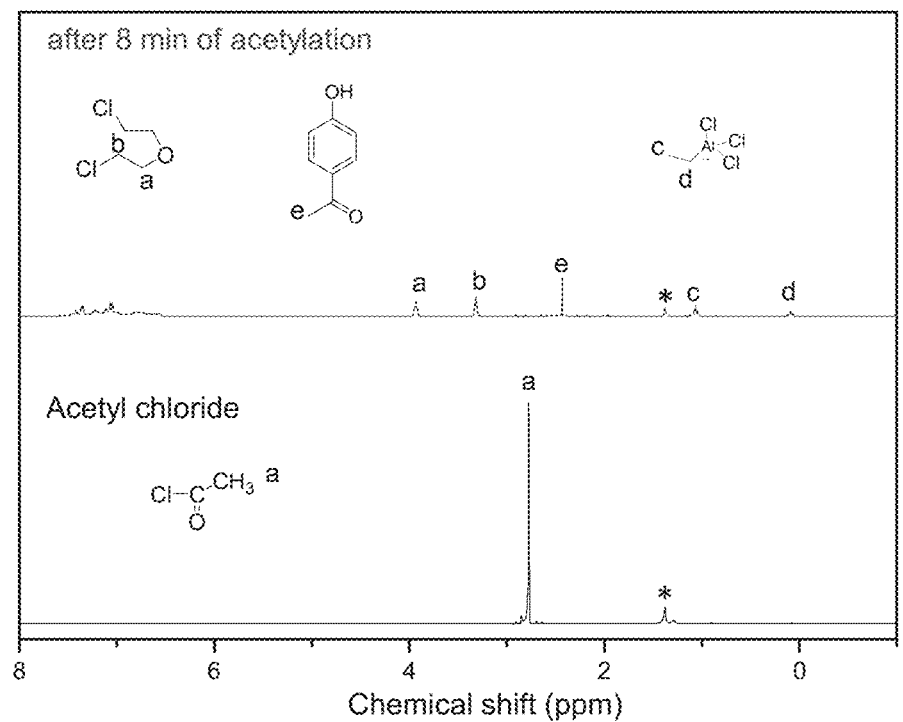
FIG. 10 shows $^1$H NMR spectra of acetyl chloride (bottom), and [EADC·CEE+AcCl] in presence of phenol after 8 min of acetylation at 25° C. in cyclohexane-d$_{12}$ (top). Initial conditions: [AcCl]=0.05 M, [EADC·CEE]=0.05 M, [Phenol]=0.05 M, [CEE]/[EADC]=1. An asterisk (*) denotes the cyclohexane-d$_{11}$H resonance.
Figure 11:
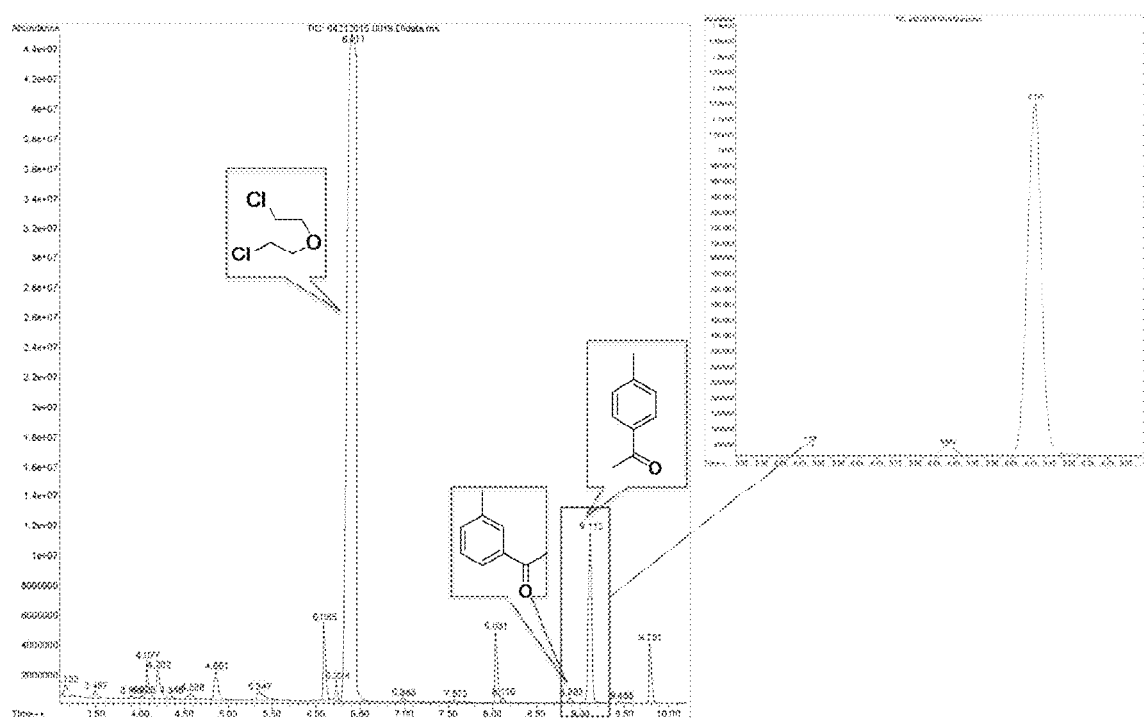
FIG. 11 is a GC trace of the product of the acetylation of toluene at 0° C. Initial conditions: [AcCl]=0.05 M, [EADC·CEE]=0.05 M, [CEE]/[EADC]=1, Temp: 0° C., EADC solution in toluene was used.
Figure 12:
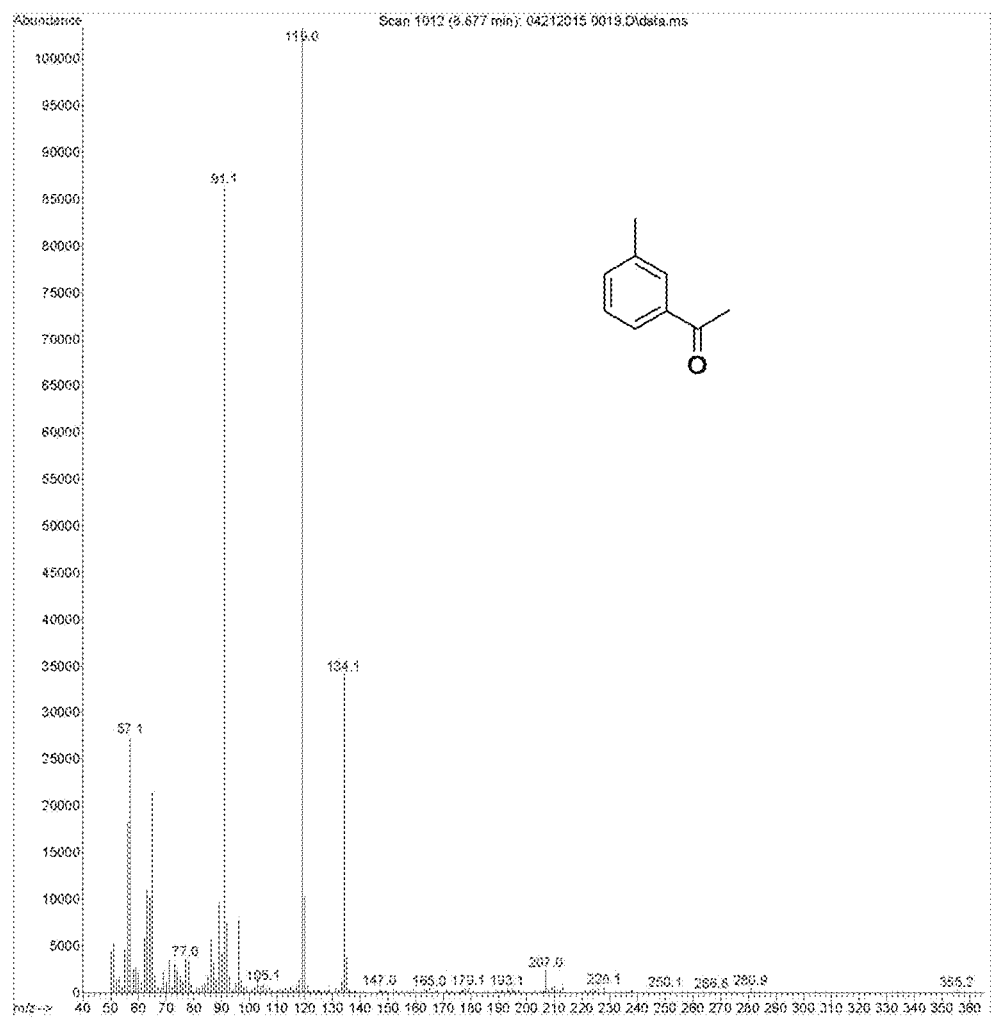
FIG. 12 is a GC-MS spectrum of the fraction at 8.8 min in the GC trace of the product of the acetylation of toluene at 0° C. Initial conditions: [AcCl]=0.05 M, [EADC·CEE]=0.05 M, [CEE]/[EADC]=1, Temp: 0° C., EADC solution in toluene was used.
Figure 13:
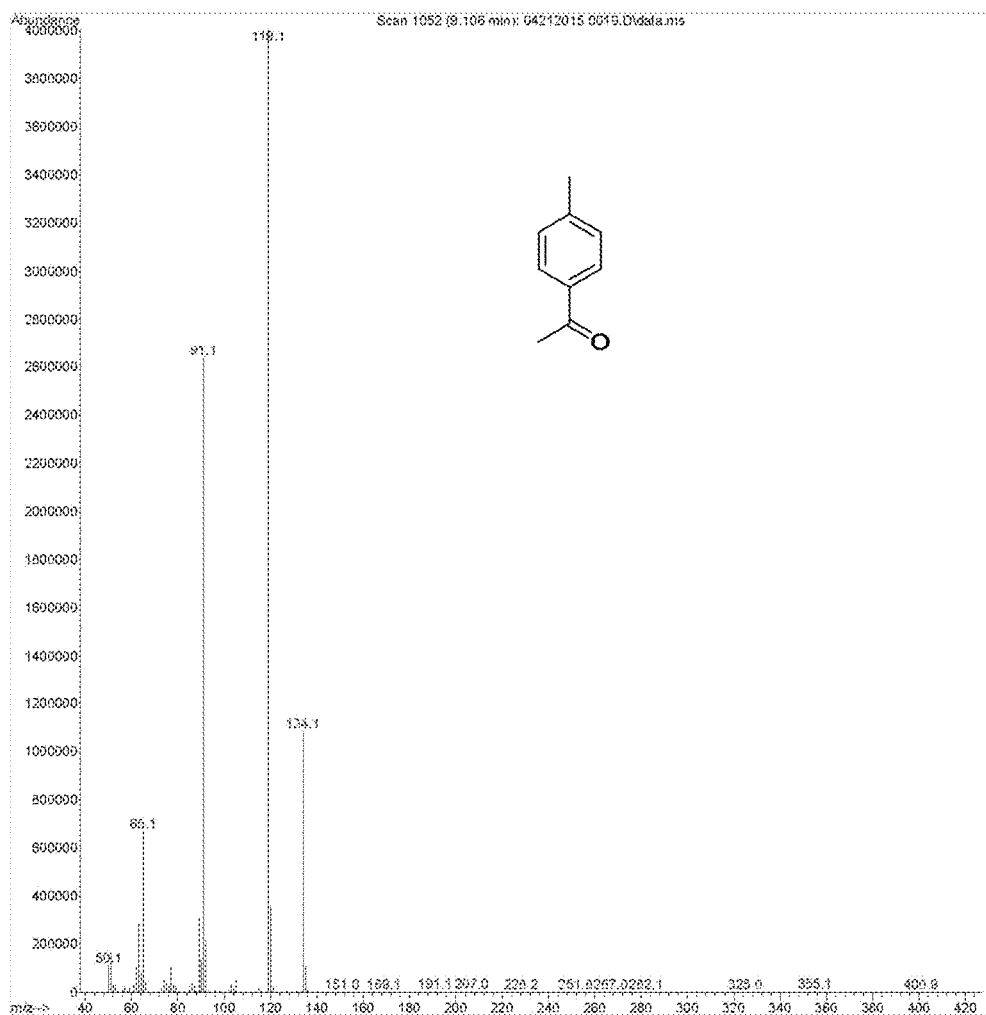
FIG. 13 is a GC-MS spectrum of the fraction at 9.1 min in the GC trace of the product of the acetylation of toluene at 0° C. Initial conditions: [AcCl]=0.05 M, [EADC·CEE]=0.05 M, [CEE]/[EADC]=1, Temp: 0° C., EADC solution in toluene was used.
Figure 14:
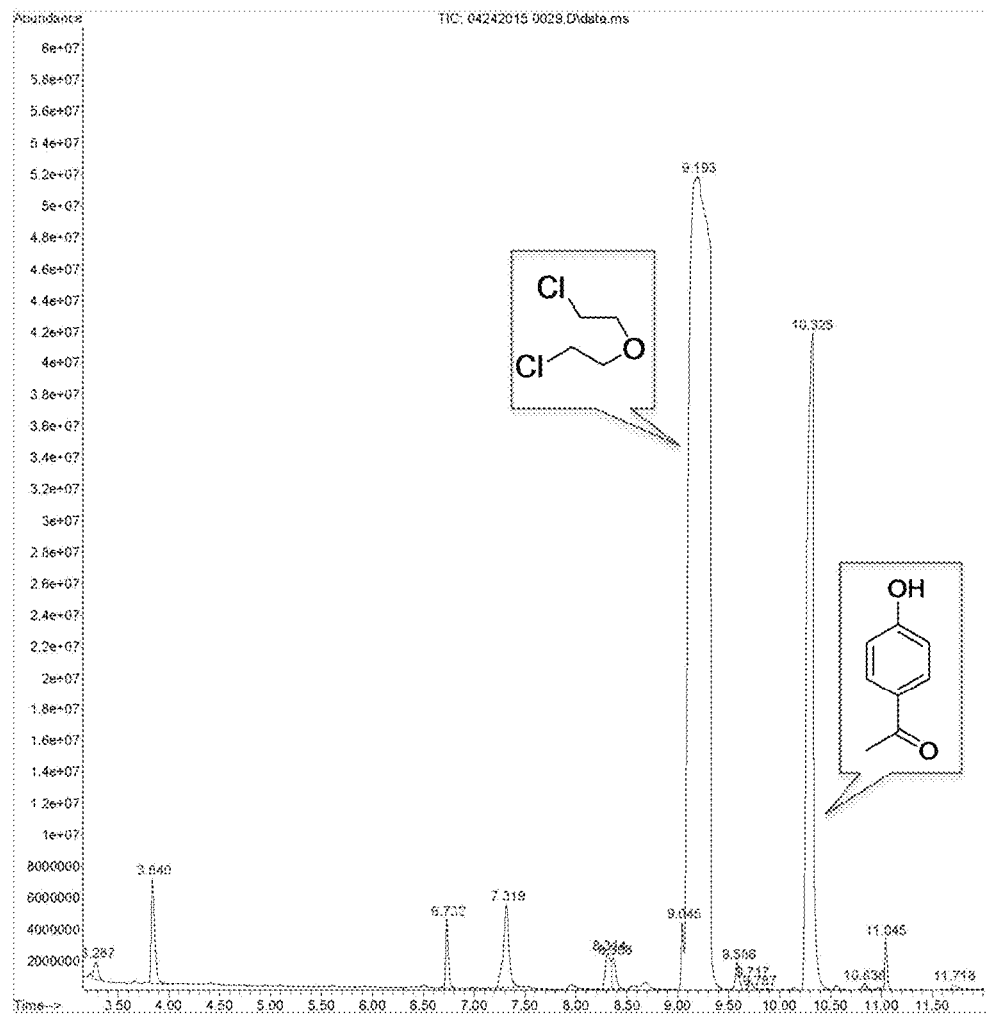
FIG. 14 is a GC trace of the product of the acetylation of phenol at 25° C. Initial conditions: [AcCl]=0.05 M, [EADC·CEE]=0.05 M, [Phenol]=0.05 M, [CEE]/[EADC]=1, Temp: 25° C., EADC solution in hexane was used.
Figure 15:
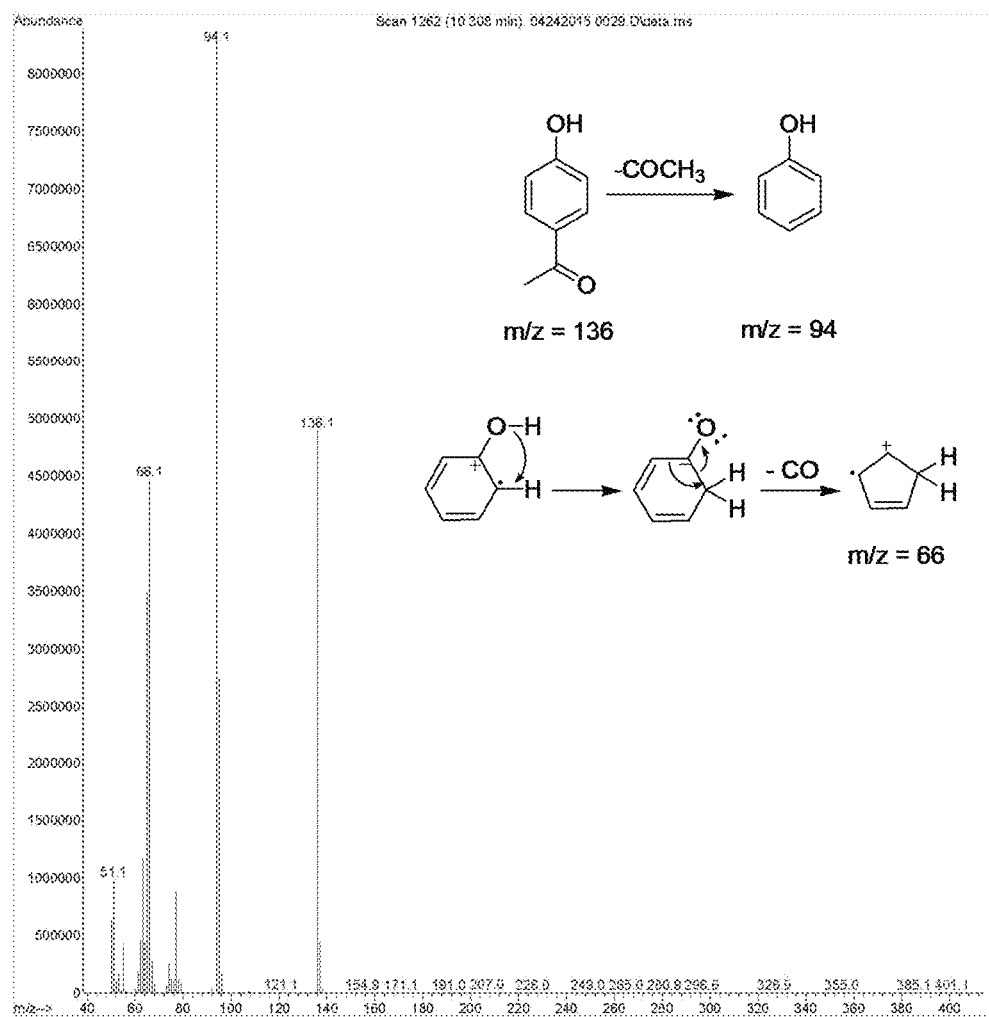
FIG. 15 is a GC-MS spectrum of the fraction at elution time 10.3 min in the GC trace of the product of the acetylation of phenol at 25° C. Initial conditions: [AcCl]=0.05 M, [EADC·CEE]=0.05 M, [Phenol]=0.05 M, [CEE]/[EADC]=1, Temp: 25° C., EADC solution in hexane was used.

Also studied was acetylation of toluene and phenol with acetyl chloride (AcCl) as a model Friedel-Crafts acylation reactions (Table 1, entries 5-6). The acetylation reactions were very fast; quantitative conversions were achieved in 8 min (FIGS. 9, 10). GC-MS analysis of the products of acetylation reveal that acetylation of toluene produces predominant para substitution (para isomer, 97%; meta isomer, 3%), whereas acetylation of phenol produces exclusively para isomer (FIGS. 11-15).

In summary, the experiments above demonstrate a simple and efficient catalyst for Friedel-Crafts alkylation/acylation reaction in non-polar solvent. The products were obtained in good yields and with high para selectivity. Furthermore, the catalyst was selective to only mono-alkylated products.

TABLE 1

Screening of reaction parameters for Friedel-Crafts alkylation/acylation reaction in nonpolar solvent.$^a$

| # | Substrate | Reagent | Catalyst | Temp. (° C.) | Time (min) | Conversion (%) | Product Composition (%) | | |
|---|---|---|---|---|---|---|---|---|---|
| | | | | | | | ortho | meta | para |
| 1 | Toluene$^b$ | t-BuCl | EADC•CEE | 0 | 120 | 96 | 0 | 5 | 95 |
| 2 | Toluene$^b$ | t-BuCl | EADC•CEE | 25 | 120 | 100 | 0 | 30 | 70 |
| 3 | Toluene$^b$ | t-BuCl | EADC | 0 | 120 | 100 | 0 | 32 | 68 |
| 4 | Phenol$^c$ | t-BuCl | EADC•CEE | 25 | 150 | 100 | 0 | 0 | 100 |
| 5 | Toluene$^b$ | AcCl | EADC•CEE | 0 | 8 | 100 | 0 | 3 | 97 |
| 6 | Phenol$^c$ | AcCl | EADC•CEE | 25 | 8 | 100 | 0 | 0 | 100 |

$^a$Reaction condition: [t-BuCl] or [AcCl] = 0.05M, [EADC•CEE] or [EADC] = 0.05M, [Phenol] = 0.05M, [CEE]/[EADC] = 1, solvent = cyclohexane-d$_{12}$,
$^b$EADC in toluene solution used;
$^c$EADC in hexane solution used. Entries 1-4: Alkylation with t-BuCl; Entries 5-6: Acetylation with AcCl.

Figure 3:
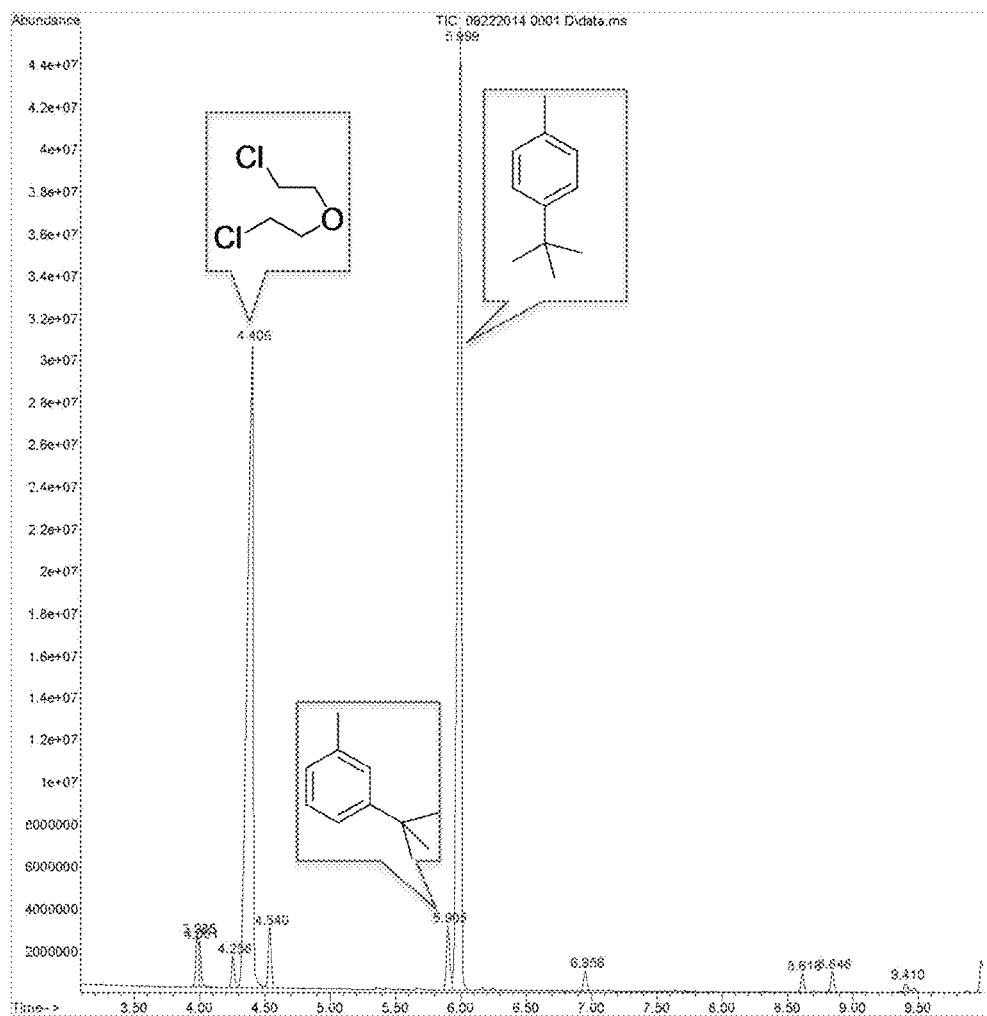
FIG. 3 shows a gas chromatography (GC) trace of the product of the t-butylation of toluene at 0° C. Initial conditions: [t-BuCl]=0.05 M, [EADC·CEE]=0.05 M, [CEE]/[EADC]=1, Temp: 0° C., EADC solution in toluene was used.
Figure 4:
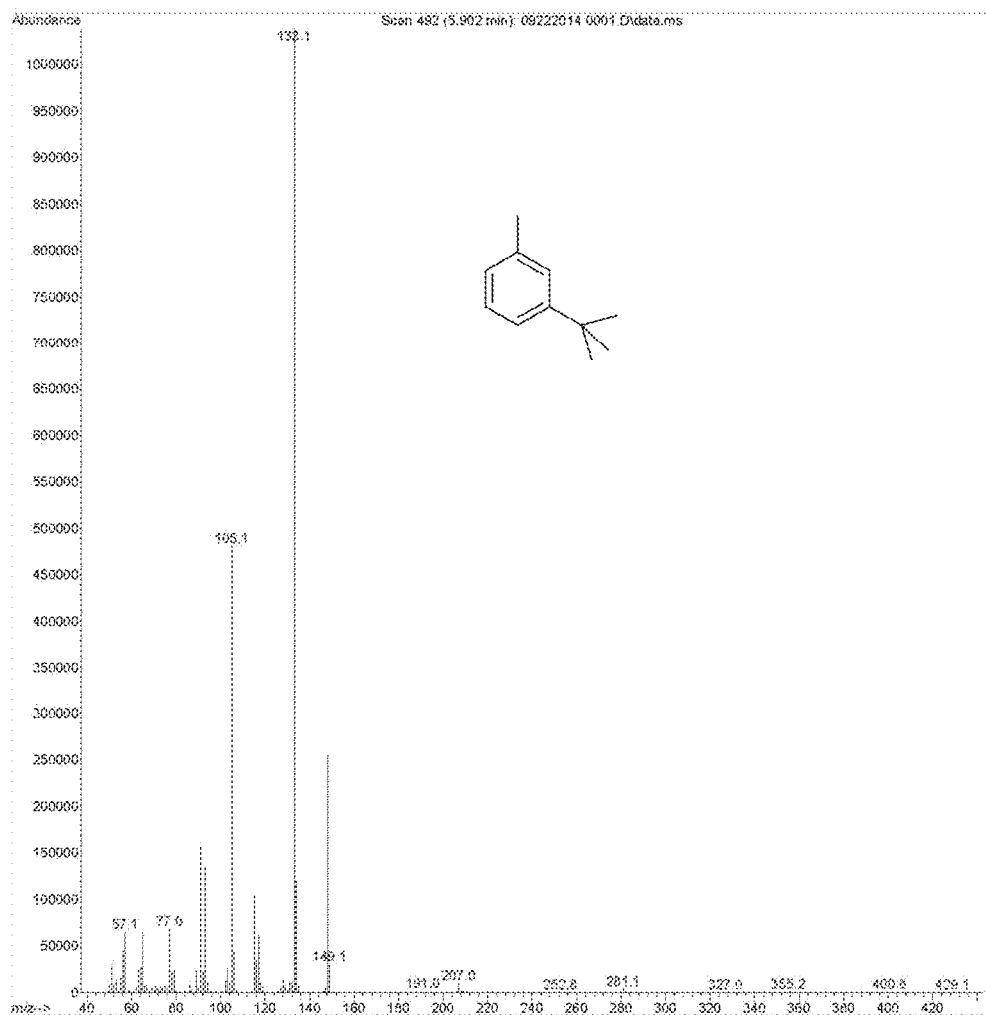
FIG. 4 is a gas chromatography-mass spectrometry (GC-MS) spectrum of the fraction at 5.90 min in the GC trace (FIG. 3) of the product of the t-butylation of toluene at 0° C. Initial conditions: [t-BuCl]=0.05 M, [EADC·CEE]=0.05 M, [CEE]/[EADC]=1, Temp: 0° C., EADC solution in toluene was used.
Figure 5:
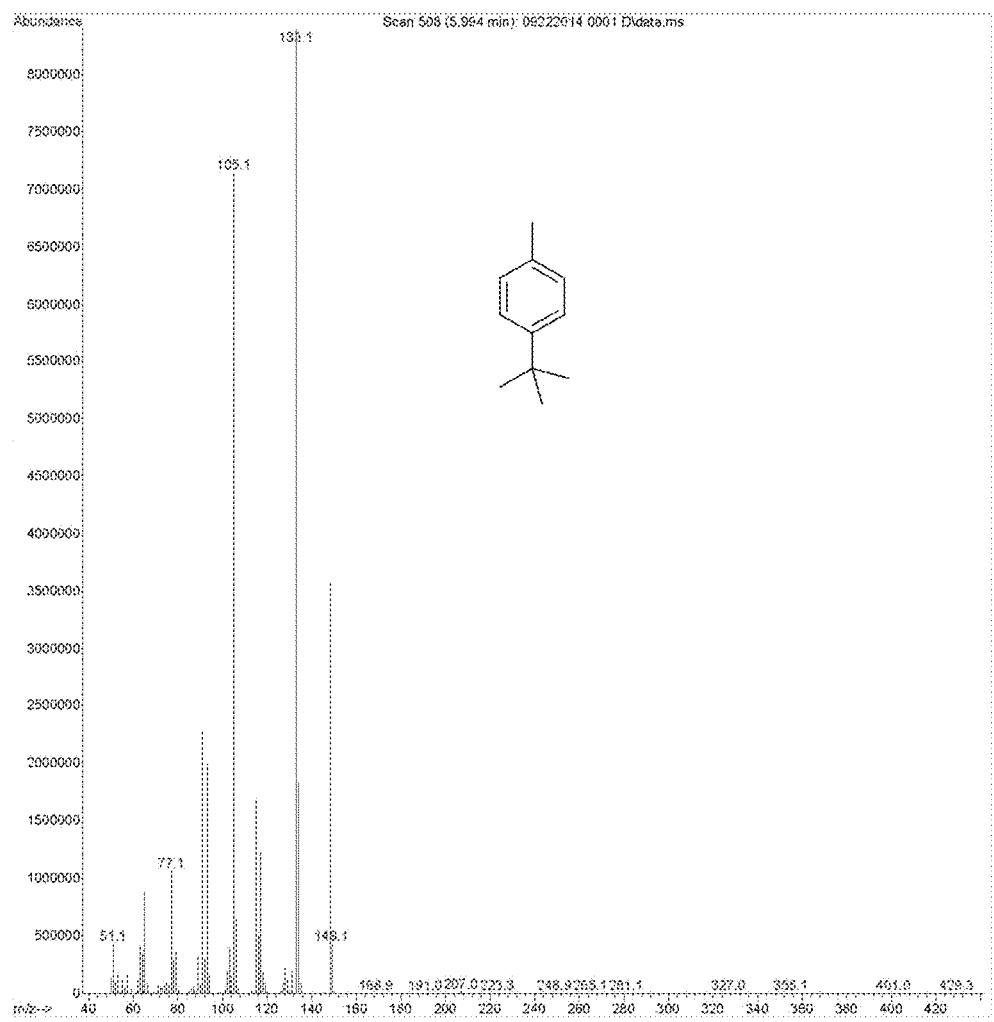
FIG. 5 is a GC-MS spectrum of the fraction at 5.99 min in the GC trace (FIG. 3) of the product of the t-butylation of toluene at 0° C. Initial conditions: [t-BuCl]=0.05 M, [EADC·CEE]=0.05 M, [CEE]/[EADC]=1, Temp: 0° C., EADC solution in toluene was used.
Figure 6:
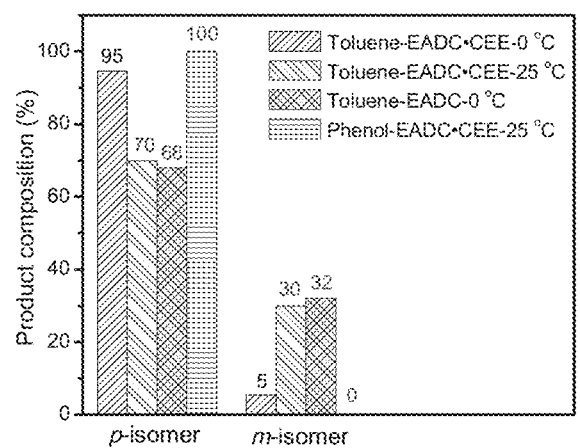
FIG. 6 is a comparison of para-selectivity of the product obtained via Friedel-Craft alkylation reaction of toluene and/or phenol in presence of t-BuCl in nonpolar solvent, determined from the GC-MS analysis.

The products of the alkylation of toluene were identified using GC-MS analysis and the results are summarized in Table 1 in terms of the aromatic product distribution after 2 hours of reaction. A GC trace of the representative alkylated products of toluene (FIG. 3) revealed the presence of two regioisomers. Based on the fragmentation pattern and the molecular ion peak of the GC-MS spectrum of the two peaks, the identity of the two isomers were confirmed as 4-tert-butyltoluene (95%) and 3-tert-butyltoluene (5%) (FIGS. 4, 5). The molar fraction of 4-tert-butyltoluene is herein defined as the para-selectivity. However, when the temperature of the alkylation reaction was raised to 25° C. from 0° C. and also when EADC is used alone as the catalyst instead of EADC·CEE complex the para selectivity decreases from 95% to ~70% (Table 1, entries 1-3). The presence of only 5% of meta isomer in the alkylation product of toluene alkylation obtained using EADC·CEE complex at 0° C. suggests a limited degree of isomerization compared to that using just EADC at 0° C. or using EADC·CEE complex at 25° C. where ~30% meta isomer was produced. Thus, our preliminary experiments indicated that use of EADC·CEE complex is necessary to obtain high para selectivity (FIG. 6).

Figure 7:
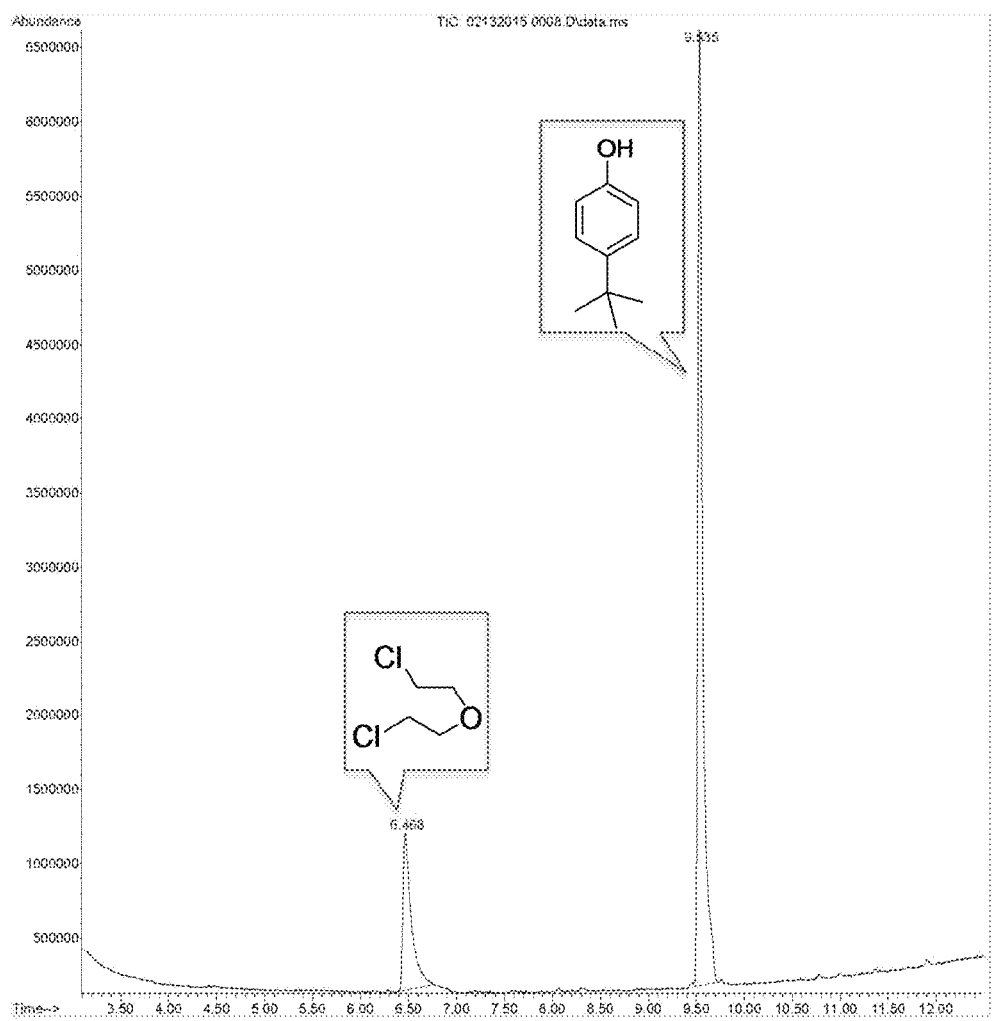
FIG. 7 is a GC trace of the product of the t-butylation of phenol at 25° C. Initial conditions: [t-BuCl]=0.05 M, [EADC·CEE]=0.05 M, [Phenol]=0.05 M, [CEE]/[EADC]=1, Temp: 25° C., EADC solution in hexane was used.
Figure 8:
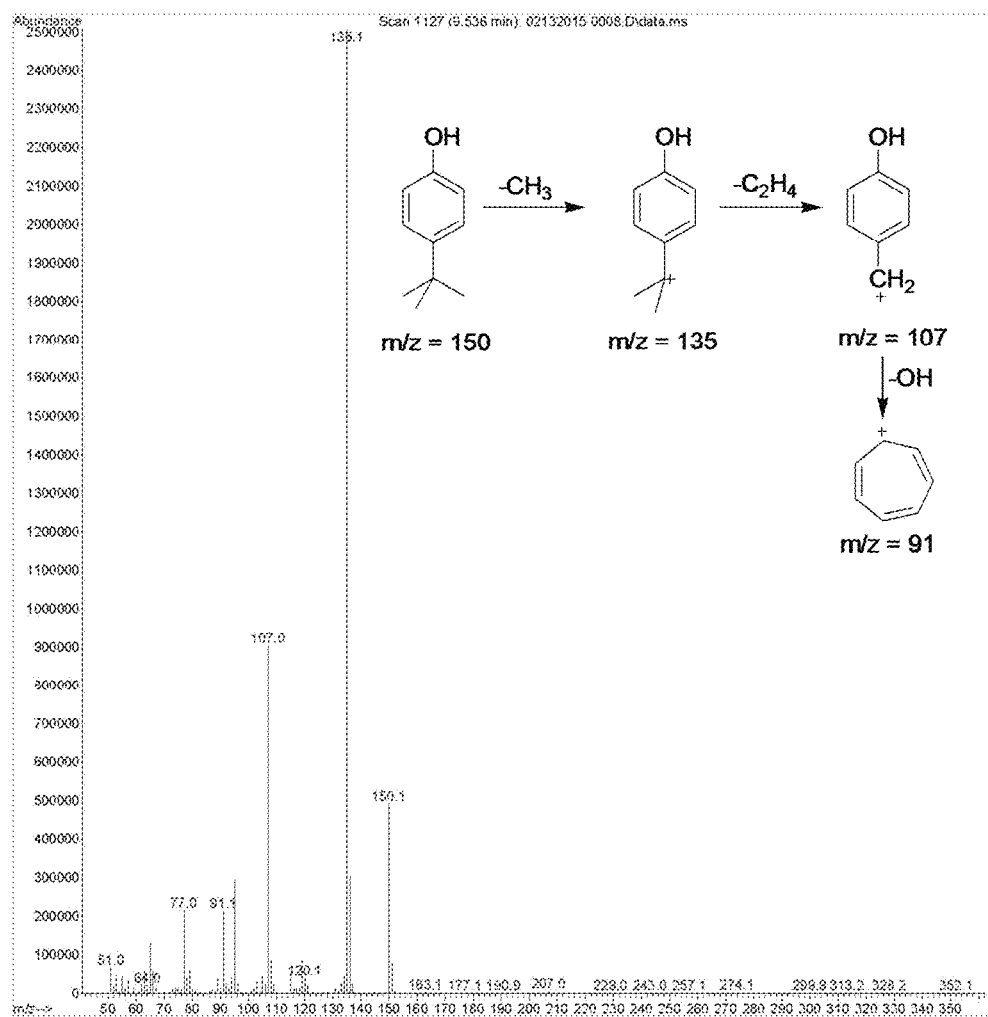
FIG. 8 is a GC-MS spectrum of the fraction at elution time 9.53 min in the GC trace (FIG. 5) of the product of the t-butylation of phenol at 25° C. Initial conditions: [t-BuCl]=0.05 M, [EADC·CEE]=0.05 M, [Phenol]=0.05 M, [CEE]/[EADC]=1, Temp: 25° C., EADC solution in hexane was used.

Alkylation of phenol using EADC·CEE complex in nonpolar solvent yielded even better para selectivity. FIG. 7 shows the GC trace of the product of alkylation of phenol using EADC·CEE complex at 25° C. These conditions yielded only a single isomer with near quantitative yield

The invention claimed is:

1. A method of alkylating or acylating an arene, the method comprising:
reacting an arene with an organic halide selected from the group consisting of unsubstituted or substituted tertiary alkyl halides, unsubstituted or substituted allyl halides, unsubstituted or substituted benzyl halides, and unsubstituted or substituted acyl halides in the presence of a catalyst and an aprotic solvent; wherein the catalyst is of formula (I)

$$MR^1{}_mX_n\cdot Z(R^2)(R^3) \qquad (I)$$

wherein
M is Al, Ga, or Fe;
R$^1$ is C$_1$-C$_{12}$ alkyl;
m is 0 or 1;
R$^2$ and R$^3$ are each independently unsubstituted or substituted C$_2$-C$_{12}$ alkyl;
each occurrence of X is independently a halogen;
n is 2 or 3;
the sum of m and n is 3; and
Z is S or O;
provided that when M is Al, then m is 1, n is 2, and R$^2$ and R$^3$ are each independently substituted with at least one electron-withdrawing group; and
provided that when M is Ga or Fe, then m is 0 and n is 3.

2. The method of claim 1, wherein the arene is an unsubstituted or substituted C$_6$-C$_{18}$ arene.

3. The method of claim 1, wherein the arene is an unsubstituted or substituted benzene.

4. The method of claim 1, wherein the arene is a mono-substituted benzene.

5. The method of claim 1, wherein the organic halide is selected from the group consisting of $C_4$-$C_{12}$ tertiary alkyl chlorides, allyl chloride, benzyl chloride, and $C_2$-$C_{12}$ acyl chlorides.

6. The method of claim 1, wherein the organic halide is t-butyl chloride or acetyl chloride.

7. The method of claim 1, wherein the aprotic solvent is an aliphatic aprotic solvent.

8. The method of claim 1, wherein the aprotic solvent is a $C_5$-$C_{12}$ alkane.

9. The method of claim 1, wherein M is Al, $R^1$ is ethyl, and each occurrence of X is chloro.

10. The method of claim 1, wherein Z is O.

11. The method of claim 1, wherein M is Al, Z is O, and the at least one electron-withdrawing group is a halogen.

12. The method of claim 1, wherein M is Al, Z is O, and the at least one electron-withdrawing group is chloro.

13. The method of claim 1, wherein M is Al, $R^1$ is ethyl, each occurrence of X is chloro, Z is O, and $R^2$ and $R^3$ are —$CH_2CH_2Cl$.

14. The method of claim 13, wherein the arene is a monoalkyl-substituted benzene, wherein the organic halide is an unsubstituted tertiary alkyl halide, wherein the solvent comprises n-hexane, and wherein said reacting is conducted at a temperature of −10 to +10° C.

* * * * *